(12) United States Patent
Kolandaivelu

(10) Patent No.: US 10,575,739 B2
(45) Date of Patent: Mar. 3, 2020

(54) AUTOMATABLE METHOD FOR DIRECTING CATHETER MOVEMENT TO TARGET ARRHYTHMIA ABLATION USING THE CARDIAC ACTIVATION SEQUENCE

(71) Applicant: THE JOHNS HOPKINS UNIVERSITY, Baltimore, MD (US)

(72) Inventor: Aravindan Kolandaivelu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1136 days.

(21) Appl. No.: 14/892,407

(22) PCT Filed: May 22, 2014

(86) PCT No.: PCT/US2014/039078
§ 371 (c)(1),
(2) Date: Nov. 19, 2015

(87) PCT Pub. No.: WO2017/190119
PCT Pub. Date: Nov. 27, 2014

(65) Prior Publication Data
US 2016/0089046 A1 Mar. 31, 2016

Related U.S. Application Data

(60) Provisional application No. 61/826,224, filed on May 22, 2013.

(51) Int. Cl.
*A61B 5/04* (2006.01)
*A61B 5/00* (2006.01)
*A61B 5/06* (2006.01)
*A61B 18/14* (2006.01)
*A61B 5/0464* (2006.01)
*A61B 18/00* (2006.01)
*A61B 90/00* (2016.01)
(Continued)

(52) U.S. Cl.
CPC ........ *A61B 5/04011* (2013.01); *A61B 5/0464* (2013.01); *A61B 5/068* (2013.01); *A61B 5/4836* (2013.01); *A61B 18/1492* (2013.01); *A61B 5/055* (2013.01); *A61B 6/032* (2013.01); *A61B 2018/00351* (2013.01); *A61B 2018/00577* (2013.01); *A61B 2018/00839* (2013.01); *A61B 2090/374* (2016.02); *A61B 2090/3762* (2016.02)

(58) Field of Classification Search
CPC combination set(s) only.
See application file for complete search history.

(56) References Cited

U.S. PATENT DOCUMENTS

2007/0060829 A1 3/2007 Pappone
2007/0219452 A1 9/2007 Cohan et al.
(Continued)

FOREIGN PATENT DOCUMENTS

WO 2012-174660 A1 12/2012

*Primary Examiner* — Scott Luan
(74) *Attorney, Agent, or Firm* — Johns Hopkins Technology Ventures

(57) ABSTRACT

The present invention is directed to an automatable method for directing electrophysiology catheter movement toward the site of arrhythmia origin using the cardiac activation sequence measured during arrhythmia and during pacing. The purpose of this method is to improve the speed and accuracy of localizing the site of arrhythmia origin for the purpose of targeting therapeutic ablation of the arrhythmia.

20 Claims, 5 Drawing Sheets

(51) Int. Cl.
    *A61B 5/055*        (2006.01)
    *A61B 6/03*         (2006.01)

(56) References Cited

U.S. PATENT DOCUMENTS

2008/0188765 A1    8/2008    Stolarski et al.
2010/0298729 A1    11/2010   Zhang et al.

AUTOMATABLE METHOD FOR DIRECTING CATHETER MOVEMENT TO TARGET ARRHYTHMIA ABLATION USING THE CARDIAC ACTIVATION SEQUENCE

CROSS-REFERENCE TO RELATED APPLICATIONS

This application is a 35 U.S.C. § 371 U.S. national entry of International Application PCT/US2014/039078, having an international filing date of May 22, 2014, which claims the benefit of U.S. Provisional Application No. 61/826,224, filed May 22, 2013, the content of each of the aforementioned applications is herein incorporated by reference in their entirety.

FIELD OF THE INVENTION

The present invention relates generally to cardiology. More particularly, the present invention relates to a method for directing catheter movement to target arrhythmia ablation.

BACKGROUND OF THE INVENTION

The target for curative arrhythmia ablation is typically near the site of earliest cardiac electrical activation during arrhythmia. However, current methods for localizing the earliest site of activation for atrial and ventricular tachycardia are inefficient, which contributes to ablation success rates of 70% or less for many of these arrhythmias.

Typically, the localization process involves point-by-point surveying of the surface of the heart using an intra-cardiac electrode catheter to search for the site of arrhythmia origin, which can be time consuming. This process is often performed by pacing at a number of points in the heart during normal rhythm until the paced cardiac activation pattern, determined by inspection of the surface and intra-cardiac electrocardiograms, "exactly" matches the cardiac activation pattern that was recorded during arrhythmia. This process is termed "pace mapping". Though getting a closely matched pace map is often not difficult, achieving an "exact" match is commonly challenging and could benefit from specific information regarding where to move the catheter to improve the pace map match.

An alternate method of mapping is to capture the global cardiac activation pattern during arrhythmia in a single heartbeat using a multi-electrode, intra-cardiac array. This method is termed "non-contact mapping". Though in concept the earliest site of arrhythmia activation can be readily located by this captured activation pattern, in practice this activation pattern may not have an exact correspondence to physical surface locations in the heart. This is particularly an issue in irregular chambers such as the left ventricle or dilated heart chambers, in which cases non-contact mapping may not be spatially accurate enough for targeting ablation and additional point-by-point contact mapping is required.

It would therefore be advantageous to provide a method that takes advantage of the accuracy of point-by-point mapping and speed of "non-contact mapping" to potentially improve the speed and accuracy of targeting ablation of arrhythmias such as atrial and ventricular tachycardia.

SUMMARY OF THE INVENTION

The foregoing needs are met, to a great extent, by the present invention, wherein in one aspect a method for localizing the site of arrhythmia includes determining the cardiac activation sequence during arrhythmia and determining the cardiac activation sequence during pacing. The method also includes calculating a difference between the cardiac activation sequence during arrhythmia and the cardiac activation sequence during pacing to obtain a vector direction of the difference. Additionally, the method includes using the vector direction to guide pacing activation pattern toward a arrhythmia activation pattern, and hence the pacing site toward the site of arrhythmia.

In accordance with an aspect of the present invention, the method further includes using local ablation therapy to treat the arrhythmia and can also include characterizing the cardiac activation sequences as a function of space. The method includes calculating the local spread of cardiac activation as a normalized local gradient of a spatial activation sequence. The method includes calculating a change in cardiac activation calculated as the difference between cardiac activation for pacing and cardiac activation for arrhythmia. Additionally, the method includes summarizing the change in cardiac activation as a single vector and integrating each component of the single vector over all points within a heart. The method also includes using a vector resultant from the integration of each component to guide catheter positioning and using changes in a direction of the vector in order to direct the catheter closer to the site of arrhythmia. The steps of the method can be incorporated into a non-contact mapping system, and a non-transitory computer readable medium is used to execute steps of the method.

In accordance with another aspect of the present invention, a system for localizing a site of arrhythmia includes a device for determining and collecting data related to a spatial activation sequence of the heart and configured to transmit the data related to the spatial activation sequence. The system also includes a non-transitory computer readable medium. The non-transitory computer readable medium is programmed to receive the data related to the spatial acquisition sequence, calculate a difference between the cardiac activation sequence during arrhythmia and the cardiac activation sequence during pacing to obtain a vector direction of the difference, and use the vector direction to guide pacing activation pattern toward a arrhythmia activation pattern, and hence the pacing site toward the site of arrhythmia.

In accordance with yet another aspect of the present invention, the device for determining and collecting data related to a spatial activation sequence of the heart takes the form of one of a group consisting of an EKG, MRI, CT, and PET scanner. The non-transitory computer readable medium is programmed to calculate the local spread of cardiac activation as a normalized local gradient of a spatial activation sequence, calculate a change in cardiac activation as the difference between cardiac activation for pacing and cardiac activation for arrhythmia, calculate the change in cardiac activation as a single vector, and integrate each component of the single vector over all points within a heart. The non-transitory computer readable medium is further programmed to calculate a vector resultant from the integration of each component to guide catheter positioning and calculate changes in a direction of the vector in order to direct the catheter closer to the site of arrhythmia. The system can also include pacing leads to treat the arrhythmia.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to an automatable method for directing electrophysiology catheter movement toward the site of arrhythmia origin using a cardiac activation sequence measured during arrhythmia and during pacing. The purpose of this method is to improve the speed and accuracy of localizing the site of arrhythmia origin for the purpose of targeting therapeutic ablation of the arrhythmia.

The cardiac electrical "activation sequence" is the time each point in the heart is first activated during a heartbeat. The first point in the heart to activate is assigned an activation time of zero. The subsequent activation sequence times, thus, reflect the spread of cardiac activation from this site of origin over time. The cardiac activation sequence during arrhythmia describes the spread of cardiac activation from the arrhythmia site of origin. Similarly, the cardiac activation sequence during pacing describes the spread of cardiac activation from the pacing site.

When the pacing site is at the location of arrhythmia origin, the difference between the spread of cardiac activation between pacing and during arrhythmia is minimized. When pacing away from the location of arrhythmia origin, the difference between the spread of cardiac activation between pacing and arrhythmia describes the direction of the difference between these activation patterns. This direction can be used to guide the pacing activation pattern toward the arrhythmia activation pattern, and hence the pacing site toward the site of arrhythmia origin. Once the pacing catheter locates the site of arrhythmia origin, local ablation therapy could be delivered around this site to treat the arrhythmia.

Figure 1:
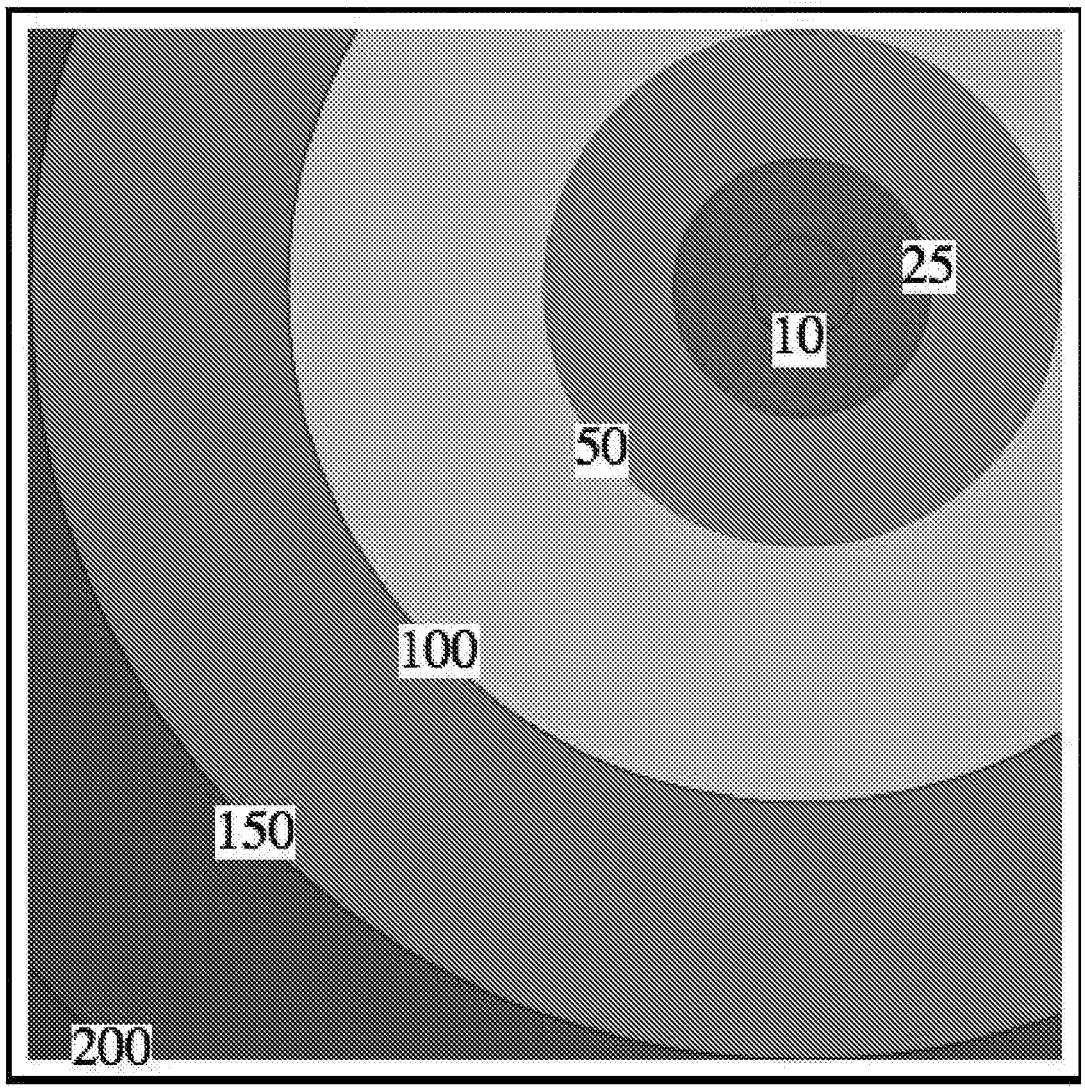
FIG. 1 illustrates a 2D example of $t_{activation}$, with activation beginning in at the center of the innermost region and spreading radially outward.

The spatial activation sequence of the heart can be acquired by many methods, such as EKG, CT scan, MRI image PET scan etc. The cardiac activation sequence can be specified as a function of space, for example: $t_{activation}$ (x, y, z) where x, y, and z are coordinates within the heart in Cartesian space and $t_{activation}$ is the time of cardiac activation at that location. FIG. 1 illustrates a 2D example of $t_{activation}$, with activation beginning in at the center of the center region and spreading radially outward.

The local spread of cardiac activation, $\vec{v}_{activation}$, can be described by, but is not limited to, the normalized local gradient of the spatial activation sequence:

$$\vec{v}_{activation}(x, y, z) = \frac{\nabla t_{activation}(x, y, z)}{\|\nabla t_{activation}(x, y, z)\|} \quad \text{(Equation 1)}$$

Figure 2:
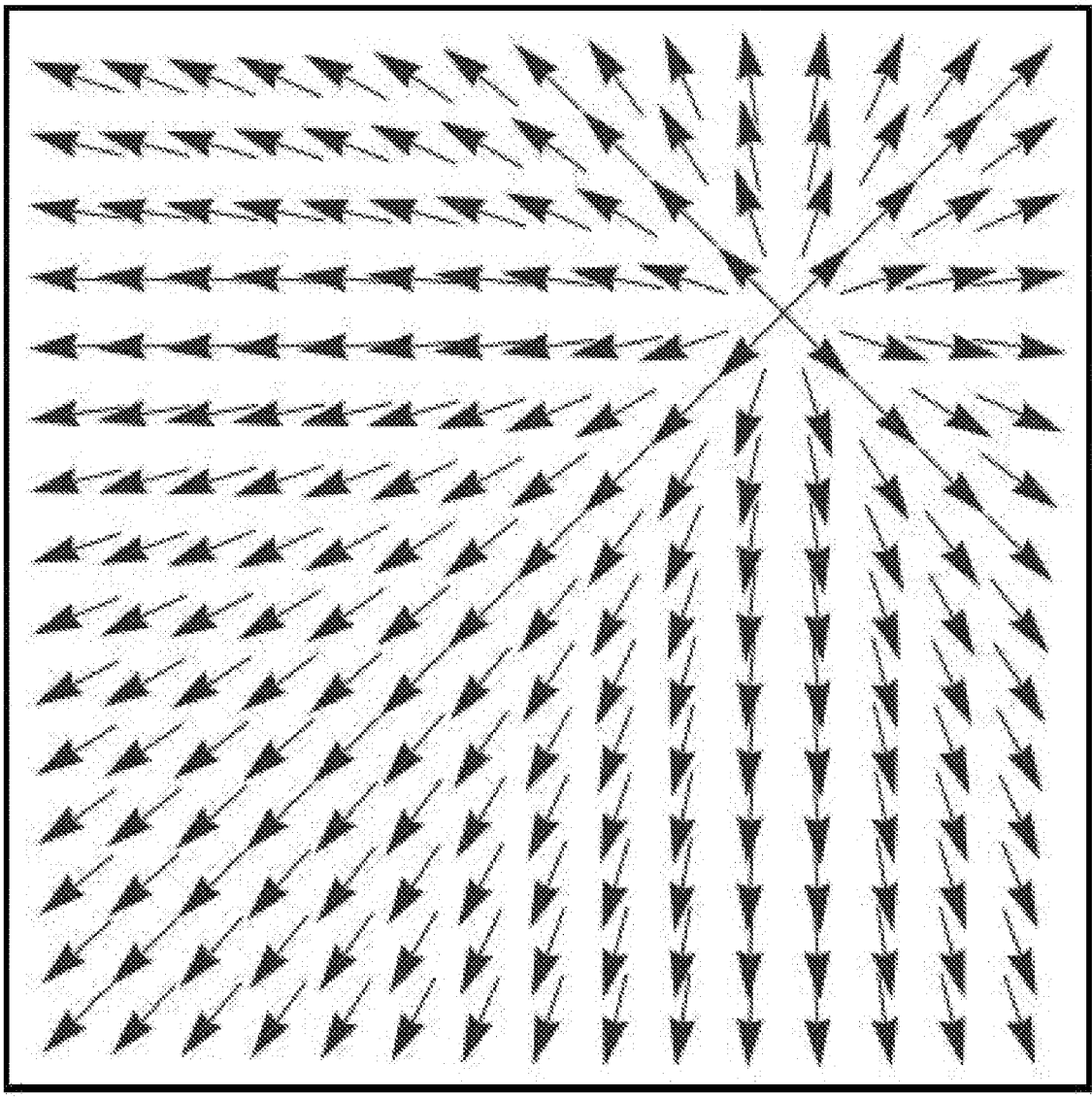
FIG. 2 shows an example of $\vec{v}_{activation}$ corresponding to the activation sequence in FIG. 1.

FIG. 2 shows an example of $\vec{v}_{activation}$ corresponding to the activation sequence in FIG. 1. The proposed system for activation sequence guided pace mapping uses some difference measure between $\vec{v}_{activation}$ between pacing and the target arrhythmia, for example simply:

$$\Delta \vec{v}_{activation}(x,y,z) = \vec{v}_{activation,paced}(x,y,z) - \vec{v}_{activation,arrythmia}(x,y,z) \quad \text{(Equation 2)}$$

Figure 3:
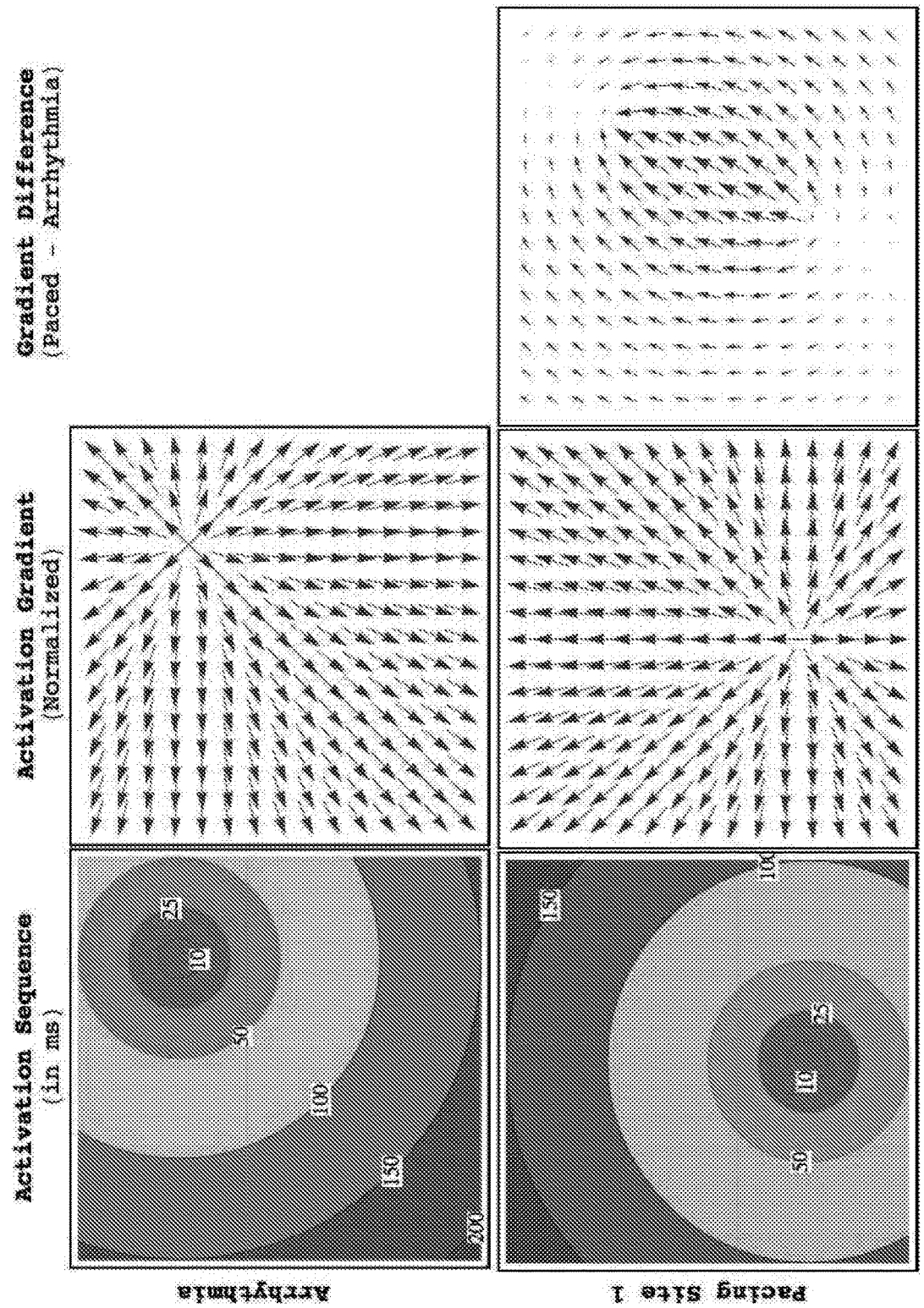
FIG. 3 illustrates examples of an activation sequence and activation gradient for an arrhythmia and a pacing site and a gradient difference for a paced arrhythmia.

FIG. 3 illustrates examples of an activation sequence and activation gradient for an arrhythmia and a pacing site and a gradient difference for a paced arrhythmia. The last column of FIG. 3 shows an example of $\Delta \vec{v}_{activation}$ calculated from the pacing and arrhythmia activation sequences specified in the first column of FIG. 3. The information contained in $\Delta \vec{v}_{activation}$ can be summarized into a single vector $\vec{v}_{map}$ by spatial integration, for example defining the components of the vector $\Delta \vec{v}_{activation}$ as:

$$\Delta \vec{v}_{activation}(x,y,z) = [\Delta i_{activation}(x,y,z), \Delta j_{activation}(x,y,z), \Delta k_{activation}(x,y,z)] \quad \text{(Equation 3)}$$

each component can be integrated over all points within the heart as:

$$i_{map} = \iiint \Delta i_{activation}(x,y,z) dx\, dy\, dz$$

$$j_{map} = \iiint \Delta j_{activation}(x,y,z) dx\, dy\, dz;$$

$$k_{map} = \iiint \Delta k_{activation}(x,y,z) dx\, dy\, dz \quad \text{(Equation 4)}$$

to generate the vector:

$$\vec{v}_{map} = [i_{map}, j_{map}, k_{map}] \quad \text{(Equation 5)}$$

Figure 4:
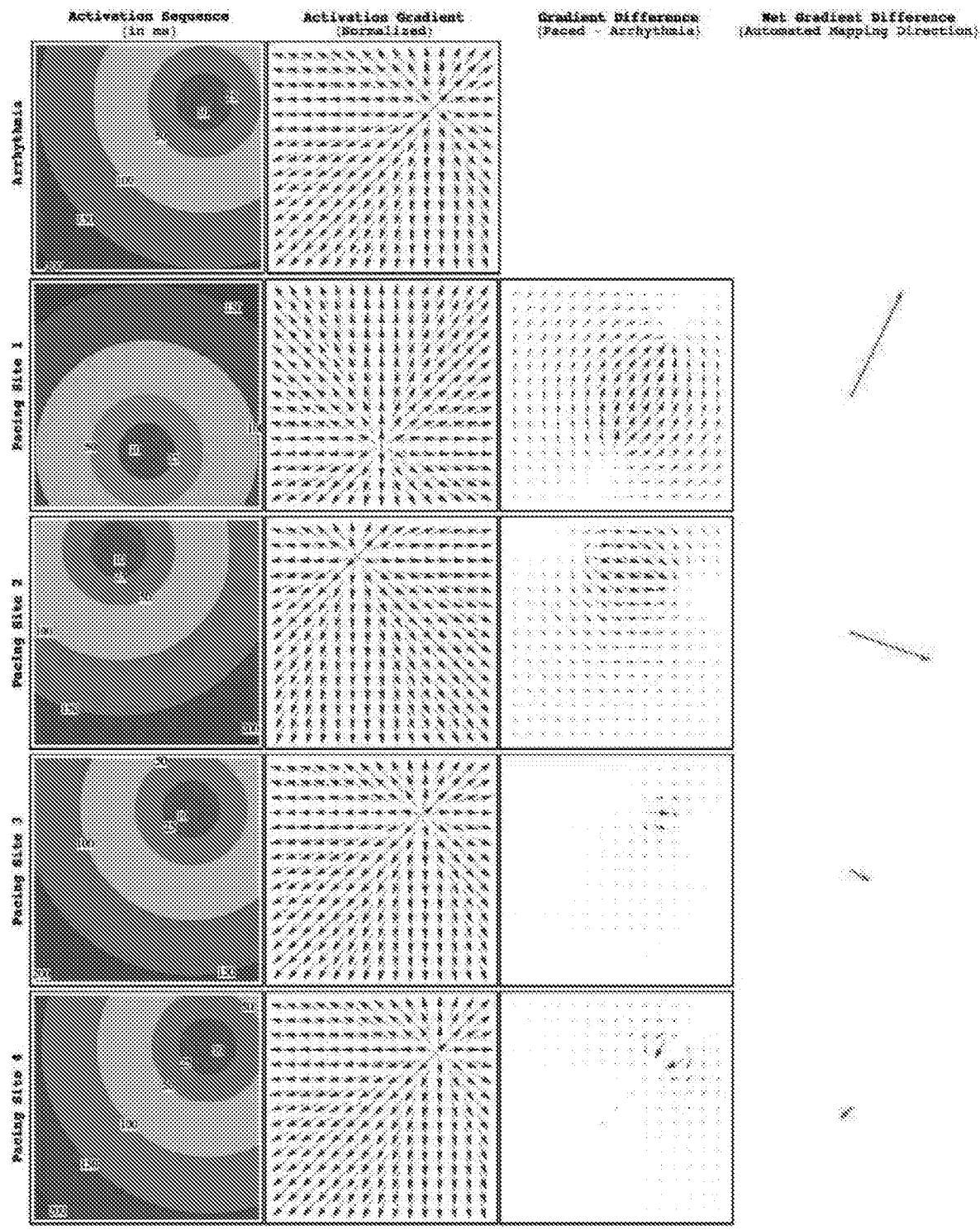
FIG. 4 illustrates examples of an activation sequence and activation gradient for an arrhythmia and pacing sites and a gradient difference and net gradient difference for paced arrhythmias at different pacing sites.

FIG. 4 illustrates examples of an activation sequence and activation gradient for an arrhythmia and pacing sites and a gradient difference and net gradient difference for paced arrhythmias at different pacing sites. The process of how this vector may be used to guide catheter positioning toward the site of arrhythmia origin is illustrated for the 2D case in FIG. 4. The first row of FIG. 4 shows an exemplary arrhythmia activation sequence and its associated $\vec{v}_{activation}$. The second row shows an exemplary pacing activation sequence, its associated $\vec{v}_{activation}$, and the resulting $\Delta \vec{v}_{activation}$ and $\vec{v}_{map}$ vector relative to the arrhythmia activation pattern. Note that the vector $\vec{v}_{map}$, disposed in the fourth row, points in the direction of the arrhythmia origin relative to the pacing site and could be used to direct catheter movement toward the arrhythmia origin. The third and fourth rows show examples of pacing from sites that are progressively closer to the arrhythmia origin. Note that the direction of $\vec{v}_{map}$ changes to reflect the direction of the arrhythmia origin relative to the new pacing sites and could be used to iteratively move the catheter closer to the arrhythmia origin. Note also that length of $\vec{v}_{map}$ shortens in parallel with closer location of the pacing sites to the arrhythmia origin and minimizing the length of $\vec{v}_{map}$ could specify when the arrhythmia origin has been reached. The fourth and fifth rows show how $\vec{v}_{map}$ may be particularly helpful for "micro-mapping" once the pacing site is close to the arrhythmia origin. The activation sequences, $t_{activation}$, for both pacing sites look similar to the arrhythmia activation sequence and it would be difficult to determine where to move the catheter based on the activation sequences alone. However, even when the pacing site is close to the arrhythmia origin the $\vec{v}_{map}$ vector provides an unambiguous indication of where to move the catheter.

Figure 5:
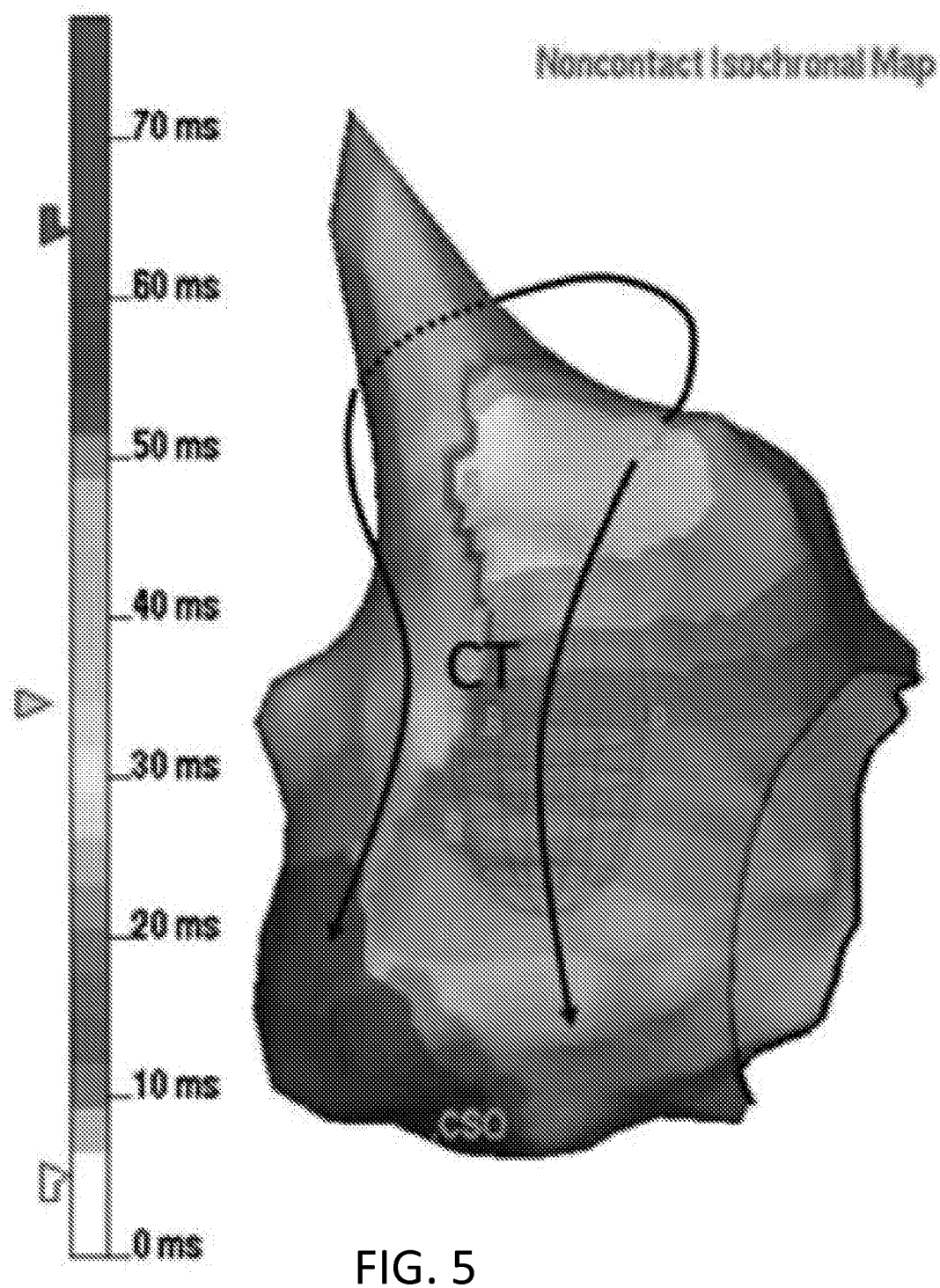
FIG. 5 illustrates an example of an EnSite non-contact activation sequence of the right atrium.

FIG. 5 illustrates an example of an EnSite non-contact activation sequence of the right atrium. The methodology described above can be readily incorporated into current "non-contact" mapping systems such as the EnSite system (St. Jude Medical). Such non-contact mapping systems can provide a 3D surface activation sequence for every heartbeat as illustrated in FIG. 5. The activation times generated by these systems are typically assigned to a vertices of a 3D mesh corresponding to points along the surface of the heart. This 3D mesh provides the $t_{activation}$ (x, y, z) function required by this method to calculate $\vec{v}_{map}$.

Because the spread of activation is constrained to the surface of a non-intersecting 3D mesh, it may be approximated by a 2D function. For simplicity of implementation instead of processing this data directly in 3D it may be preferable to first transform the 3D surface activation sequence, $t_{activation}$ (x, y, z) into a 2D planar activation sequence, $t_{activation}$ (m, n), of the form showed in FIG. 1. This can be done using standard methods such as those used to transform the spherical earth onto flat maps. The process explicitly illustrated in FIGS. 1 to 4 may then be applied to the resulting $t_{activation}$ (m, n) to obtain a 2D $\vec{v}_{map}$ vector, which still has enough information to indicate which direction to move the catheter along the original 3D surface.

In addition to deriving the 3D $t_{activation}$ (x, y, z) or 2D $t_{activation}$ (m, n) cardiac activation sequence from non-contact mapping, the activation sequence information could be obtained from other sources including but not limited to body-surface potential mapping techniques and imaging based mechanical activation mapping. This method could be applied to 3D/transmural mapping if information about the transmural activation sequence is provided, for example by combining information from body surface potential derived estimation of the epicardial activation sequence with non-contact mapping estimation of the endocardial activation sequence or using imaging.

In addition, the gradient operator $\nabla t_{activation}$ (x, y, z) used to calculate $\vec{v}_{activation}$, in Equation 1, may need to have local constraints to avoid crossing discontinuities in conduction that occur along lines of conduction block as illustrated in the activation sequence show in FIG. 5. In this figure, the line of conduction block is displayed as a solid line (without arrow heads). In addition, in some cases it may be useful to constrain the region of integration used to calculate $\vec{v}_{map}$, Equations 4 and 5, to a smaller region around the pacing location. This may be useful in the setting of more complex cardiac activation sequences, as are seen in reentrant arrhythmias.

Though the method was illustrated in the context of localizing focal ectopic cardiac activation, the method may have utility for reentrant arrhythmias such as scar-mediated tachycardia. In this case, the direction suggested for catheter movement might be expected to lead from the entry point of the reentry circuit back toward the exit point of the circuit, which corresponds to the site of earliest cardiac activation, and remains a target for ablation.

In addition, the proposed method may permit use of smaller non-contact mapping arrays, which are easier to place and manipulate in the cardiac chamber. A limitation of current non-contact mapping systems is that the accuracy of activation location information degrades at distances more than 4 cm from the center of the electrode array, so a relatively large array is used. The proposed method relies on the relative activation sequences between pacing and arrhythmia rather than the accuracy of the physical location determined by the mapping system and so could potentially improve the mapping accuracy of smaller intra-cardiac electrode arrays which could make the non-contact mapping technique more generally applicable.

Though this method was discussed in the context of "dense" measures of spatial activation sequence, the method could be applied to estimated spatial activation sequences that are derived, for example, from a limited set of surface electrodes set such as potentially even the standard 10 electrodes used for used for clinical 12—lead ECG. Because standard body surface potential mapping (BSP) requires more than a hundred electrodes and non-contact mapping requires additional vascular access and introduction of another invasive catheter, these methods are not part of routine electrophysiology practice. However, a continuous 12-lead ECG recording is part of every electro physiology study and the ability to utilize spatial cardiac activation derived from this information, or with some additional electrodes as necessary to improve estimated BSP accuracy, would make the proposed method easier to integrate into standard clinical practice.

Because this method provides unambiguous information regarding the direction of catheter movement, i.e. the vector $\vec{v}_{map}$, as well as criterion for when the target site of earliest arrhythmia activation has been reached, i.e. the magnitude of the vector $\vec{v}_{map}$, in principle this method could be applied to control remote catheter manipulation systems to automatically localize favorable sites for ablation.

The method of the present invention can be carried out with the aid of a non-transitory computer readable medium programmed to execute steps and equations associated with the method. The non-transitory computer readable medium can be read and executed by any computing device known to or conceivable by one of skill in the art, such as a personal computer, imaging computing station, EKG computing station, tablet, smartphone, phablet, server, etc. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard, disk, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, or any other suitable data transmission means known to or conceivable by one of skill in the art.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for localizing the site of arrhythmia comprising:
    determining the cardiac activation sequence during arrhythmia;
    determining the cardiac activation sequence during pacing;
    calculating a difference between the cardiac activation sequence during arrhythmia and the cardiac activation sequence during pacing to obtain a vector direction of the difference; and
    using the vector direction to guide pacing activation pattern toward an arrhythmia activation pattern, and hence the pacing site toward the site of arrhythmia.

2. The method of claim 1 further comprising using local ablation therapy to treat the arrhythmia.

3. The method of claim 1 further comprising characterizing the cardiac activation as a function of space.

4. The method of claim 1 further comprising calculating the local spread of cardiac activation as a normalized local gradient of a spatial activation sequence.

5. The method of claim 1 further comprising calculating a change in cardiac activation calculated as the difference between cardiac activation for pacing and cardiac activation for arrhythmia.

6. The method of claim 5 further comprising summarizing the change in cardiac activation as a single vector.

7. The method of claim 6 further comprising integrating each component of the single vector over all points within a heart.

8. The method of claim 7 further comprising using a vector resultant from the integration of each component to guide catheter positioning.

9. The method of claim 8 further comprising using changes in a direction of the vector in order to direct the catheter closer to the site of arrhythmia.

10. The method of claim 1 further comprising incorporating steps of the method into a non-contact mapping system.

11. The method of claim 1 further comprising programming a non-transitory computer readable medium to execute steps of the method.

12. A system for localizing a site of arrhythmia comprising:
    a device for determining and collecting data related to a spatial activation sequence of the heart and configured to transmit the data related to the spatial activation sequence;
    a non-transitory computer readable medium programmed to:
    receive the data related to the spatial acquisition sequence;
    calculate a difference between the cardiac activation sequence during arrhythmia and the cardiac activation sequence during pacing to obtain a vector direction of the difference; and
    use the vector direction to guide pacing activation pattern toward an arrhythmia activation pattern, and hence the pacing site toward the site of arrhythmia.

13. The system of claim 12 wherein the device for determining and collecting data related to a spatial activation sequence of the heart takes the form of one of a group consisting of an EKG, MRI, CT, and PET scanner.

14. The system of claim 12 further comprising programming the non-transitory computer readable medium to calculate the local spread of cardiac activation as a normalized local gradient of a spatial activation sequence.

15. The system of claim 12 further comprising programming the non-transitory computer readable medium to calculate a change in cardiac activation as the difference between cardiac activation for pacing and cardiac activation for arrhythmia.

16. The system of claim 15 further comprising programming the non-transitory computer readable medium to calculate the change in cardiac activation as a single vector.

17. The system of claim 16 further comprising programming the non-transitory computer readable medium to integrate each component of the single vector over all points within a heart.

18. The system of claim 17 further comprising programming the non-transitory computer readable medium to calculate a vector resultant from the integration of each component to guide catheter positioning.

19. The system of claim 18 further comprising programming the non-transitory computer readable medium to calculate changes in a direction of the vector in order to direct the catheter closer to the site of arrhythmia.

20. The system of claim 12 further comprising pacing leads to treat the arrhythmia.

* * * * *